Jan. 20, 1948. C. A. SANDERSON Plant Pat. 782
GRAPE VINE
Filed July 16, 1946
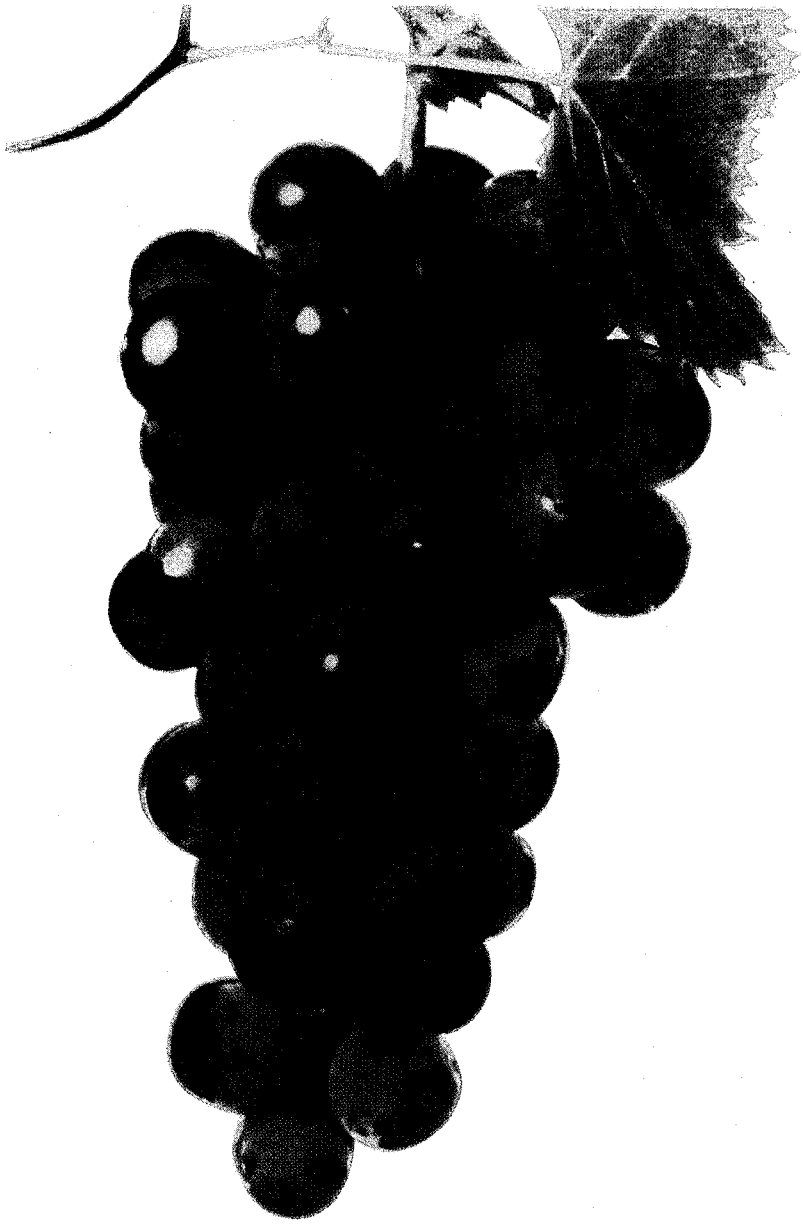
Inventor
C. A. Sanderson
By Robbins Robb
Attorneys Patented Jan. 20, 1948

Plant Pat. 782

UNITED STATES PATENT OFFICE

782

GRAPEVINE

Chester A. Sanderson, Glendale, Ariz.

Application July 16, 1946, Serial No. 683,843

1 Claim. (Cl. 47—62)

The present discovery relates to a new and distinct variety of grape vine, a chance seedling which I found growing in my vineyard between a Guava and a Feijoa. The dominating characteristics of novelty lie in the extreme vigor of its growth and unusual, mild, sweet flavor of its fruit.

To illustrate its vigorous habit of growth, it may be noted that in the first season after discovery, the vine made a growth of about fifteen feet, while other seedlings growing under comparable conditions grew only twelve to eighteen inches. Upon making this observation, the seedling was removed and planted to itself the early part of the year. It bore no fruit that year, but made a good growth of about twenty foot spread. In the next season of following year, it bore only a few bunches of grapes but doubled its growth.

These grapes had a dark slipskin, somewhat akin to Concord type, and were of good flavor, medium round in shape.

In the following year, still under careful observation, the vine reached a sixty-foot growth, advancing to one hundred foot spread in the following season, and a heavy hedge up to ten feet at each end.

Each of the preceding years I pruned the vine back some and this season it stands at about one hundred ten feet spread and has on it, as nearly as I can determine, about 800 clusters of grapes, after thinning them out about 50%, of oblong shape in distinction to the short clusters of the Concord type. This remarkable habit of growth thoroughly demonstrated to me the vigor of the new variety.

In flavor, it is decidedly mild and delicious as compared with the Concord variety, approaching more that of the black Muscat.

The trunk of the vine is approximately eleven inches in circumference with rough or shaggy bark, a size which is not so great considering its enormous growth.

The foliage resembles the Concord and Golden Muscat though the leaves are not quite as large as the Concord's.

The nodes are about six inches apart and strong. The canes remain green longer than those of the Concord before turning brown and are heavier than Concords; the tendrils are much heavier and stronger. The hardiness of this new variety is outstanding when compared with twenty different varieties grown in the same vineyard.

As for the fruit, the grapes are of medium size, blackish with maroon cast; slip skin, with mild, sweet flavor and medium firm, juicy flesh; formed in clusters about seven inches long, quite compact and uniform. The peduncle is quite heavy and strong; the clusters are all shaded by comparatively dense foliage.

By way of comparison with the variety of Campbell Early, the characteristics of which are given in Hedrick, "Systematic Pomology," published 1925, by MacMillan Co., N. Y. (at pages 398–399), it may be stated that while the tendrils on both varieties are bifid and trifid, in the case of Campbell they are short while in my variety they are long and strong. In Campbell, the under surface of the leaves is bronze, whereas in mine they are greenish gray. Campbell's petiolar sinus is shallow and wide, in mine deep and narrow or closed together sometimes; Campbell's lateral sinus is wide or of notch shape, while in mine it is deep and narrow; the berries of Campbell are oval and dark purplish-black, and in mine they are round and dark with maroon cast. The seeds are small in my grape and generally less in number than in Campbell.

This new variety has been asexually reproduced from root cuttings and in all progeny, the characteristics herebefore noted come true to form.

In the drawing, the figure illustrates a specimen of a cluster of the berries and specimen of the foliage.

By way of summary of the characteristics, the following is a detailed description of this new variety.

(Observations herein given were made of specimens grown on a ranch near Glendale, Arizona.)

Plant: Medium large; vigorous; dense; vary productive; regular bearer; deciduous.

Environment: Sun. Climate—dry.

Canes: Medium; rough; stout. Color—brown.

Tendrils: Very tough and stout; appropriate for trellis.

New shoots: Color—green with slight tinge of pink on leaf stems.

Foliage:

*Leaves.*—Abundant; medium large; heavy; rugose. Texture—upper side: Green and has crepe effect; under side: Light or silver green with prominent veins. Shape—About 50% round or without lobes; the remainder having rather deep sinuses forming a 3-lobe leaf structure, with acute apex, round base and serrate margin. Color — mature: Upper surface — dark green; under surface—silver green. Measurements—9 inches from base to apex; 8 inches in breadth. Color—young: Upper surface—golden brown mixed with light green; under surface—silver gray. Variation—not much.

Mid-rib: Heavy. Upper side—smooth; under side—smooth.

Flowers: Abundant. Clusters—abundant. Length of flowering season—about two weeks. Shape and size of cluster—medium and oblong; average seven inches long. Peduncle—medium length; heavy.

*Before calyx breaks.*—Size—medium. Form—globular.

Bloom:

*Flowering began.*—About April 15th.

*Flowering peak.*—May 1st.

Reproductive organs:

*Stamens.*—Medium number.

*Filaments.*—Medium length.

*Pollen.*—Moderate.

Fruit:

*Maturity when described.*—August 1st, at the same time as the Western Concord, or about two weeks later than Campbell Early.

*Size of berry.*—Medium.

*Diameter.*—¾ inch.

*Transverse base to apex.*—¾ inch.

*Number of clusters.*—800.

*Number of berries to cluster.*—72.

*Form of berries.*—Uniform; globose.

*Number of seeds per berry.*—2 to 3 small seeds.

*Productiveness.*—Very productive, with clusters quite compact.

*Skin.*—Slip skin.

*Tomentum.*—Wanting.

*Color.*—Dark with slight maroon cast. At a short distance it appears black.

*Ripening began.*—August 1st.

*Ripening peak.*—August 20th.

*Ripening end.*—September 28th.

*Cluster ripens.*—Even.

*Texture.*—Medium soft.

*Flavor.*—Mild; sweet.

*Aroma.*—Distinct.

*Eating quality.*—Excellent

*Juice quality.*—Excellent.

Seed:

*Size.*—Medium.

*Length.*—¼ inch.

*Form.*—Obovoid.

Use: Juice; jelly.

Keeping quality: Good.

Shipping quality: Good. Berry does hold well on stem on picking.

I claim:

A new and distinct variety of grape vine, characterized dominantly as to novelty by its outstanding habit of vigorous growth and hardiness; color of and mild, sweet flavor of its berries; great productivity; and form and abundance of its foliage and fruit clusters, substantially as shown and described.

CHESTER A. SANDERSON.

REFERENCES CITED

The following references are of record in the file of this patent:

Hedrick, "Systematic Pomology," published 1925 by MacMillan Co., N. Y., pages 398 and 399, description of Campbell Early.